(12) United States Patent
Sternik

(10) Patent No.: US 10,292,689 B2
(45) Date of Patent: May 21, 2019

(54) BODY PART REPOSITIONING APPARATUS AND METHOD

(75) Inventor: Leonid Sternik, Kiryat Ono (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 19 days.

(21) Appl. No.: 14/232,573

(22) PCT Filed: Jul. 9, 2012

(86) PCT No.: PCT/IL2012/000278
§ 371 (c)(1),
(2), (4) Date: Jan. 13, 2014

(87) PCT Pub. No.: WO2013/008231
PCT Pub. Date: Jan. 17, 2013

(65) Prior Publication Data
US 2014/0171733 A1   Jun. 19, 2014

Related U.S. Application Data

(60) Provisional application No. 61/457,928, filed on Jul. 11, 2011.

(30) Foreign Application Priority Data

Mar. 19, 2012 (IL) .......................... 218737

(51) Int. Cl.
*A61B 17/064* (2006.01)
*A61B 17/00* (2006.01)
(Continued)

(52) U.S. Cl.
CPC ...... *A61B 17/00234* (2013.01); *A61B 17/064* (2013.01); *A61B 17/083* (2013.01);
(Continued)

(58) Field of Classification Search
CPC ........ A61B 17/12013; A61B 17/12022; A61B 17/12031; A61B 17/12122;
(Continued)

(56) References Cited

U.S. PATENT DOCUMENTS

| 2,235,350 A | 3/1941 | Anderson |
| 5,224,497 A * | 7/1993 | Ehlers ................ A61B 17/0057 |
| | | 128/898 |

(Continued)

FOREIGN PATENT DOCUMENTS

| EP | 1579823 | 9/2005 |
| WO | WO-2008020975 A2 | 2/2008 |

(Continued)

OTHER PUBLICATIONS

International Search Report of PCT/IL2012/000278 dated Nov. 11, 2012.
(Continued)

*Primary Examiner* — Darwin P Erezo
*Assistant Examiner* — Erich Herbermann

(57) ABSTRACT

A device for manipulating a body part, comprises: a) an elongated guide instrument provided with a tip suitable to be positioned in close juxtaposition with a tissue at a desired location of the said body part; and b) a suction channel terminating in or near said tip.

10 Claims, 10 Drawing Sheets

(51) Int. Cl.
*A61B 17/12* (2006.01)
*A61B 17/30* (2006.01)
*A61B 17/08* (2006.01)
*A61B 17/221* (2006.01)

(52) U.S. Cl.
CPC .. *A61B 17/12013* (2013.01); *A61B 17/12122* (2013.01); *A61B 17/12131* (2013.01); *A61B 17/221* (2013.01); *A61B 17/30* (2013.01); *A61B 17/00491* (2013.01); *A61B 2017/00243* (2013.01); *A61B 2017/308* (2013.01); *A61B 2217/005* (2013.01)

(58) Field of Classification Search
CPC ........ A61B 17/00234; A61B 17/00491; A61B 17/064; A61B 2017/308; A61B 17/221
USPC ........................................ 606/139, 151, 157
See application file for complete search history.

(56) References Cited

U.S. PATENT DOCUMENTS

| | | | |
|---|---|---|---|
| 5,792,153 | A | 8/1998 | Swain et al. |
| 6,383,198 | B1 * | 5/2002 | Hamilton ......... A61B 17/22031 606/110 |
| 7,427,279 | B2 | 9/2008 | Frazier et al. |
| 8,647,367 | B2 | 2/2014 | Kassab et al. |
| 8,784,469 | B2 | 7/2014 | Kassab |
| 2001/0041914 | A1 | 11/2001 | Frazier et al. |
| 2003/0158563 | A1 | 8/2003 | McClellan et al. |
| 2004/0044364 | A1 * | 3/2004 | DeVries ............... A61B 17/064 606/213 |
| 2005/0021016 | A1 | 1/2005 | Malecki et al. |
| 2007/0043344 | A1 | 2/2007 | McAuley |
| 2007/0083082 | A1 | 4/2007 | Kiser et al. |
| 2007/0225734 | A1 | 9/2007 | Bell et al. |
| 2008/0033241 | A1 | 2/2008 | Peh et al. |
| 2008/0294175 | A1 | 11/2008 | Bardsley et al. |
| 2008/0312664 | A1 * | 12/2008 | Bardsley .......... A61B 17/12009 606/142 |
| 2009/0326518 | A1 * | 12/2009 | Rabin ................ A61B 17/0218 606/1 |
| 2010/0145361 | A1 | 6/2010 | Francischelli et al. |
| 2010/0191279 | A1 | 7/2010 | Kassab et al. |
| 2010/0312256 | A1 | 12/2010 | Kassab et al. |
| 2011/0082495 | A1 | 4/2011 | Ruiz |
| 2012/0035622 | A1 | 2/2012 | Kiser |
| 2014/0018831 | A1 | 1/2014 | Kassab et al. |
| 2014/0171733 | A1 | 6/2014 | Sternik |
| 2016/0106437 | A1 | 4/2016 | van der Burg et al. |
| 2017/0065283 | A9 | 3/2017 | Kassab et al. |

FOREIGN PATENT DOCUMENTS

| | | |
|---|---|---|
| WO | WO-2012103556 A2 | 8/2012 |
| WO | WO 2018/178979 | 10/2018 |

OTHER PUBLICATIONS

Supplementary European Search Report and the European Search Opinion dated Feb. 27, 2015 From the European Patent Office Re. Application No. 12811116.8. (8 Pages).
Communication Pursuant to Article 94(3) EPC dated Apr. 19, 2017 From the European Patent Office Re. Application No. 12811116.8. (9 Pages).
International Preliminary Report on Patentability dated Jan. 14, 2014 From the International Bureau of WIPO Re. Application No. PCT/IL2012/000278. (10 Pages).
Written Opinion dated Nov. 11, 2012 From the International Searching Authority Re. Application No. PCT/IL2012/000278. (9 Pages).
Written Opinion dated Oct. 23, 2012 From the International Searching Authority Re. Application No. PCT/IL2012/000278. (8 Pages).
International Search Report and the Written Opinion dated Aug. 14, 2018 From the International Searching Authority Re. Application No. PCT/IL2018/050353. (22 Pages).
Invitation to Pay Additional Fees, Communication Relating to the Results of the Partial International Search and the Provisional Opinion dated Jun. 20, 2018 From the International Searching Authority Re. Application No. PCT/IL2018/050353. (16 Pages).
Boston Scientific "Reducing the Risk of Stroke in Atrial Fibrillation With the Watchman™ Left Atrial Appendage (LAA) Closure Device", Boston Scientific, SH-282105-AA, Poster Leaflet, 2 P., Nov. 2014.
Hu et al. "Device-Based Approach to Prevention of Stroke in Atrial Fibrillation", The Journal of Innovations in Cardiac Rhythm Management, 6: 2038-2050, Jun. 2015.
Kreidieh et al. "Left Atrial Appendage Remodeling After Lariat Left Atrial Appendage Ligation", Circulation Arrhythm Electrophysiology, 8(6): 1351-1358, Published Online Oct. 20, 2015.
Omran "Left Atrial Appendage Anatomy: The LAA is Unique as a Fingerprint, How to Close Those Successfully?", Euro PCR 2016, Slide Show, 37 P., 2016.
Piccini et al. "Left Atrial Appendage Occlusion: Rationale, Evidence, Devices, and Patient Selection", European Heart Journal, EHW330: 1-9, Advance Access Publication Sep. 13, 2016.
Communication Pursuant to Article 94(3) EPC dated Oct. 31, 2018 From the European Patent Office Re.

* cited by examiner

BODY PART REPOSITIONING APPARATUS AND METHOD

FIELD OF THE INVENTION

The present invention relates to the evagination and the grasping, fixating and fastening of a part in the human body (referred to hereinafter as "repositioning"). More particularly, the invention relates to a device that permits to perform a procedure that repositions the left atrial appendage of the heart.

BACKGROUND OF THE INVENTION

Atrial rhythm abnormalities are associated with the development of blood clots in the atrial chamber, which can result in the formation of thrombus and emboli which may (among other things) cause brain stroke. The left atrial appendage ("LAA") is particularly susceptible to clot formation. Several approaches were developed to reduce the risk of clot formation in the LAA, mainly consisting in physically separating or occluding the LAA from the left atrium. Said devices reduce the risk of blood clots in the LAA and/or obstruct or filter the flow of clots from the LAA into the atrium. One example of the separation devices are permanently-implanted occluders. Permanently-implanted occluders (e.g., Watchman®) are usually introduced transseptally up to the LAA by a delivery cathether and then the device is anchored at the desired location by fixation barbs or other methods.

An example of such an occlusion device is shown in FIG. 1, which illustrates how a Watchman occlusion device 100 is introduced through the right atrium 101 and transseptally catheterized, as shown at 103, to reach the LLA 102 (image taken from http://www.hkma.org/english/cme/clinicalcase/201003a_set.htm).

A second example of physical separation of LAA is described in U.S. Pat. No. 7,427,279, which discloses a closure catheter comprising deployable tissue anchors. The device is to be inserted up to the LAA. Once located properly, the anchors are deployed into the surrounding tissue and draw the tissue radially inwardly to close the LAA cavity.

A third example of physical separation of LAA are permanently implanted clip (e.g., The AtriClip™ LAA Exclusion System—http://www.atricure.com) which contains an LAA Clip for open occlusion of the heart's left atrial appendage. The Clip is pre-loaded on a disposable Clip applier. Said clips are located extraluminally, and require open-chest surgery.

Blood clot formation in the LAA is managed also by anticoagulant therapies, such as Warfarin (Coumadin). Said therapies cause significant complications in 1-2% of patients a year.

Although a variety of procedures has been suggested for overcoming the problem, all procedures known in the art are either long and complex, or present severe dangers resulting from perforation of the cardiac (left atrial and LAA) wall, or from the voluntary or involuntary removal of portions of the LAA, and many present both drawbacks. Therefore, so far the art has failed to provide a simple and safe method to perform the closure of the LAA, and no attempts have been made to evaginate it as a stage of a closure procedure.

It is an object of the invention to provide a method and apparatus for repositioning a body part.

It is another object of the invention to provide a device that permits to perform a medical procedure by which there is evagination and then constant fixation in the left atrium of the LAA, which can be safely performed without the danger of damaging the LAA tissue.

It is yet another object of the invention to provide a device suitable for carrying out a procedure at the end of which the repositioned LAA is covered by not-thrombogenic endocardium and cannot harbor blood clots.

Other objectives and advantages of the invention will become apparent as the description proceeds.

SUMMARY OF THE INVENTION

The invention in one aspect relates to a device for manipulating a body part, comprising:
  a) an elongated guide instrument provided with a tip suitable to be positioned in close juxtaposition with a tissue at a desired location of the said body part; and
  b) a suction channel terminating in or near said tip.

In one aspect, said manipulating comprises repositioning the body part.

According to one embodiment of the invention the suction channel terminates in a concave holder, such as, e.g., a holder selected from a cup, a cone, or other semi-spherical shape. The holder is preferably—but not limitatevely—made of flexible material.

The device of the invention may further integrally comprise fastening means, or fastening means may be provided separately. In one embodiment of the invention the fastening means are actuatable from the elongated guide instrument. In another embodiment of the invention the fastening means comprise, at or near its proximal end, a string or the like flexible looped element. The flexible looped element may be conveniently provided in its pre-deployed position, such that it is looped around the axis of the elongated guide instrument.

In one embodiment of the invention the fastening means comprise a clipping or clamping fastener. In another embodiment of the invention the fastening means comprise a staple.

In a particularly interesting embodiment of the invention the device is suitable to reposition a body part, which is the left atrial appendage of a heart.

The suction channel can be also used for aspiring blood clots, especially those located in the LAA.

In another embodiment of the invention the device is suitable to secure and isolate polyps in the GI tract.

Also encompassed by the invention is a device, which is coupled to fastening means, which are not integral therewith. In one embodiment of such device, the fastening means comprise filling means suitable to fill the void created in the outer part of a heart, by the repositioning of the left atrial appendage of the heart. Suitable filling means comprise, e.g., a biocompatible glue.

The invention is also directed to a method for repositioning a body part, comprising positioning an elongated guide instrument provided with a tip in close juxtaposition with a tissue at a desired location, wherein said guide instrument is provided with a suction channel terminating in or near said tip and with fastening means actuatable from said elongated guide instrument.

Figure 2:
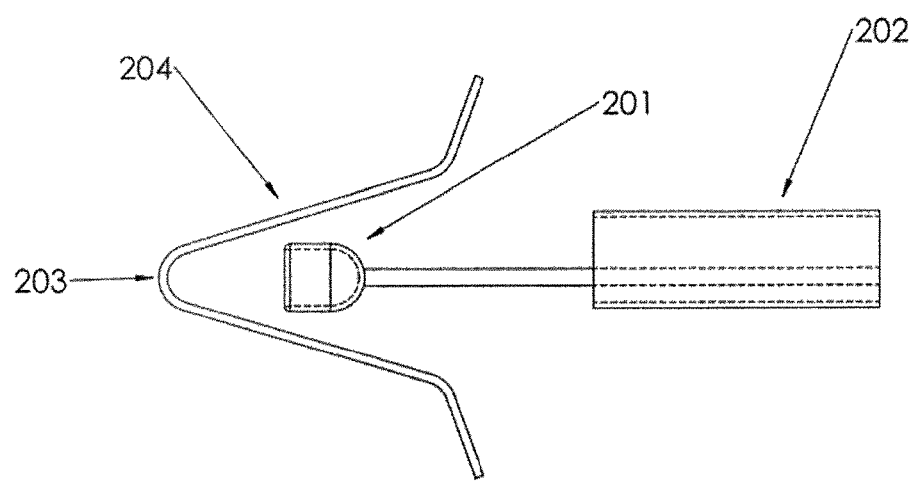
Figure 3:
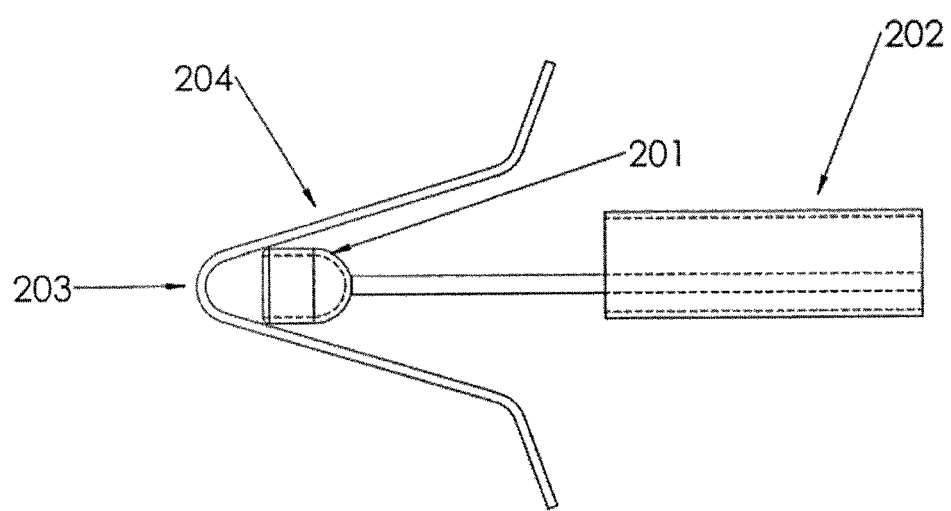
Figure 4A:
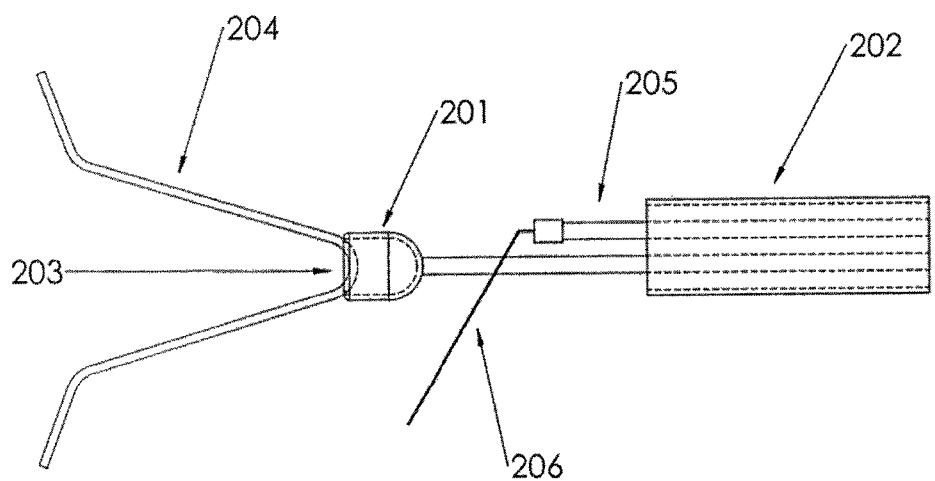
Figure 4B:
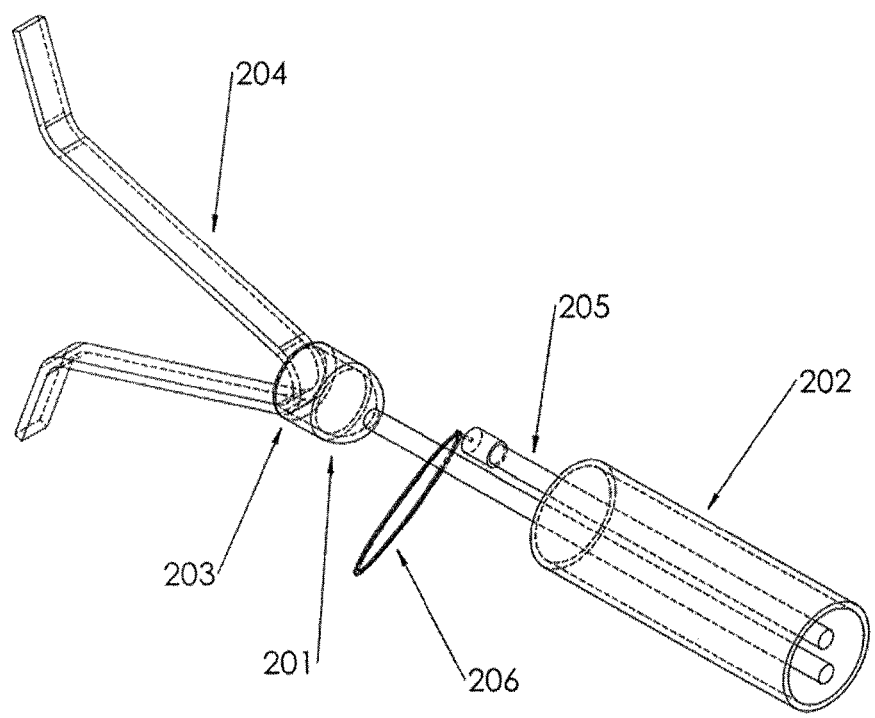
Figure 5A:
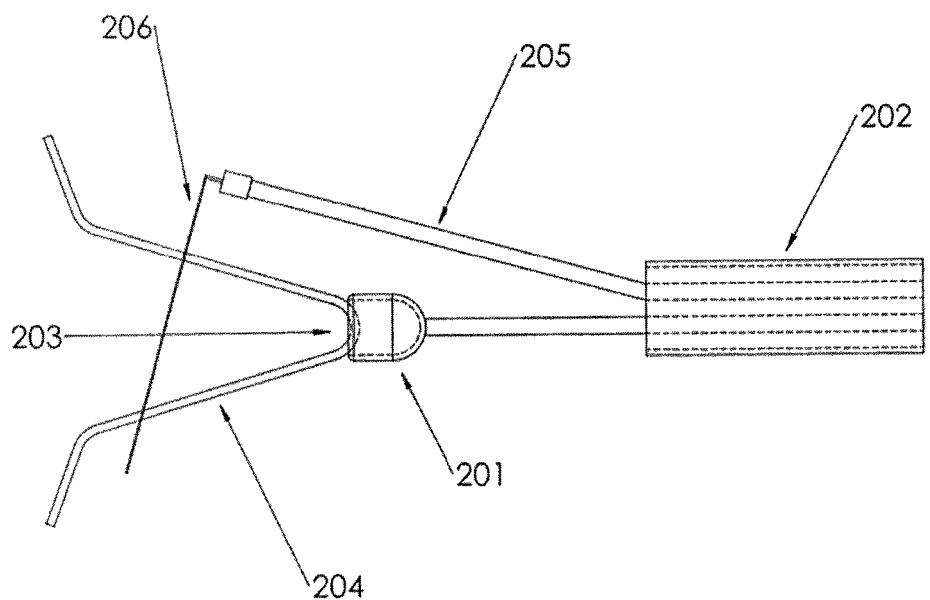
Figure 5B:
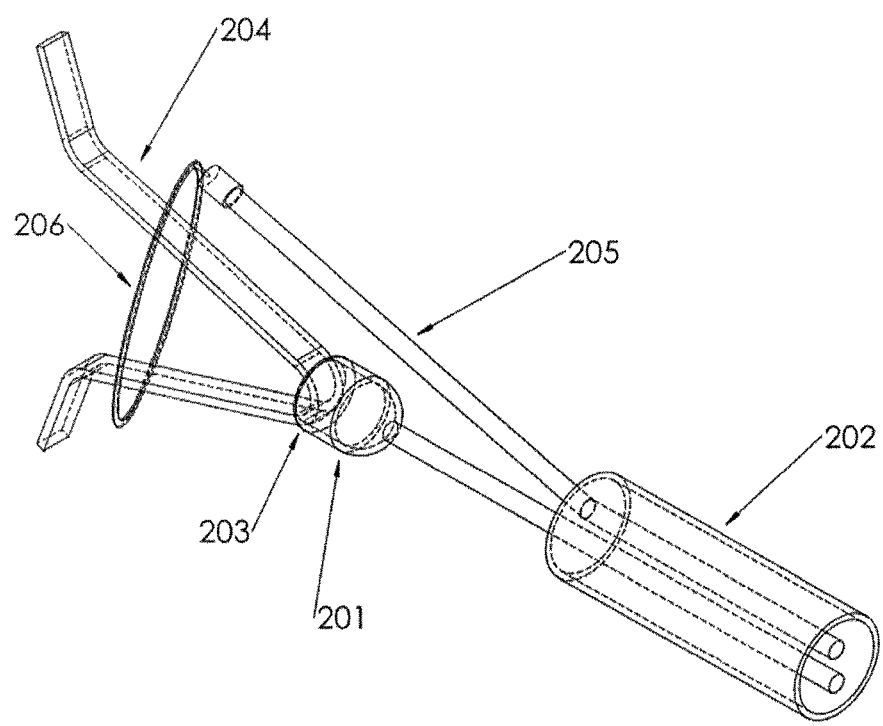
Figure 6A:
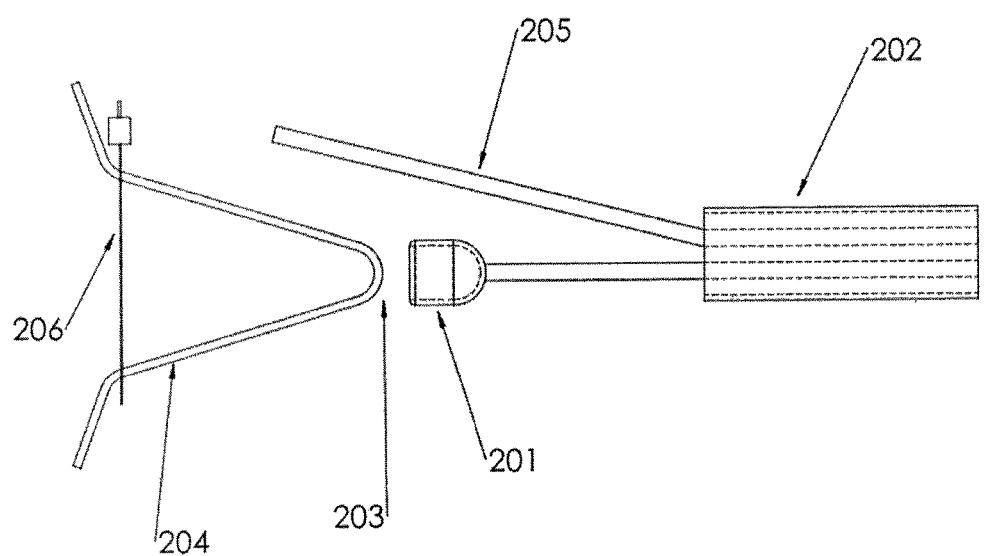
Figure 6B:
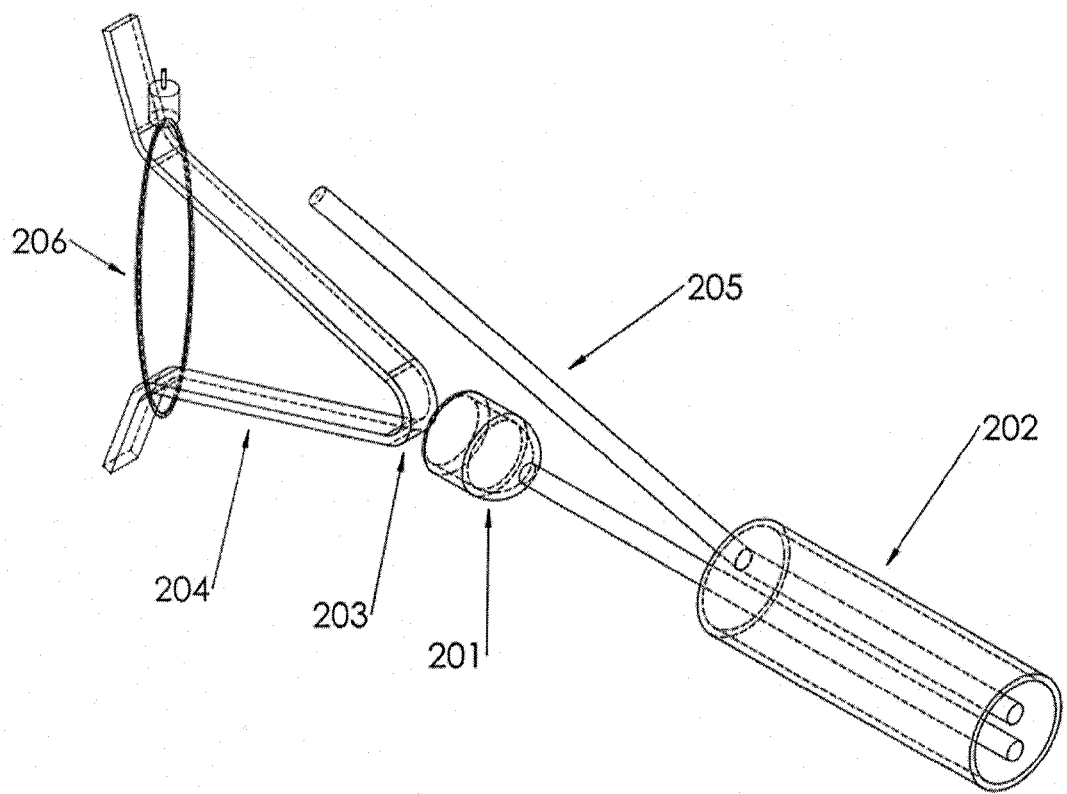

All other figures schematically illustrates the operation of a device according to the invention, wherein:

FIG. 2 illustrates the anatomical positioning of the guide instrument into the left atrium before entering the LAA and after inflating the suction catheter;

FIG. 3 illustrates the anatomical positioning of the guide instrument into the LAA before activating the suction device;

FIGS. 4a and 4b illustrate the reshaping of the LAA after pulling back the guide instrument;

FIGS. 5a and 5b illustrate the application of an open clip to the base of the LAA;

FIGS. 6a and 6b schematically illustrate the closed clip, lasso or suture; and

Figure 7:
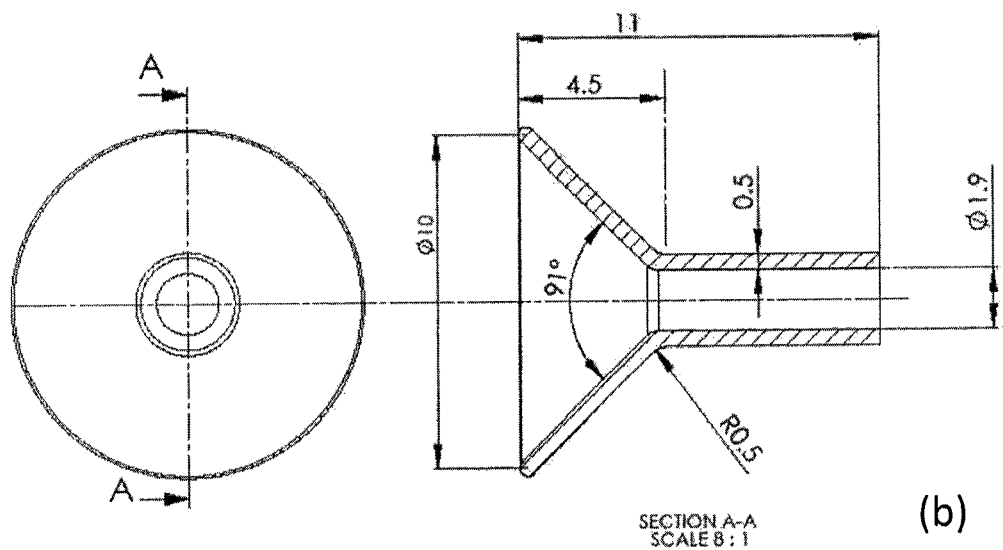
Figure 7:
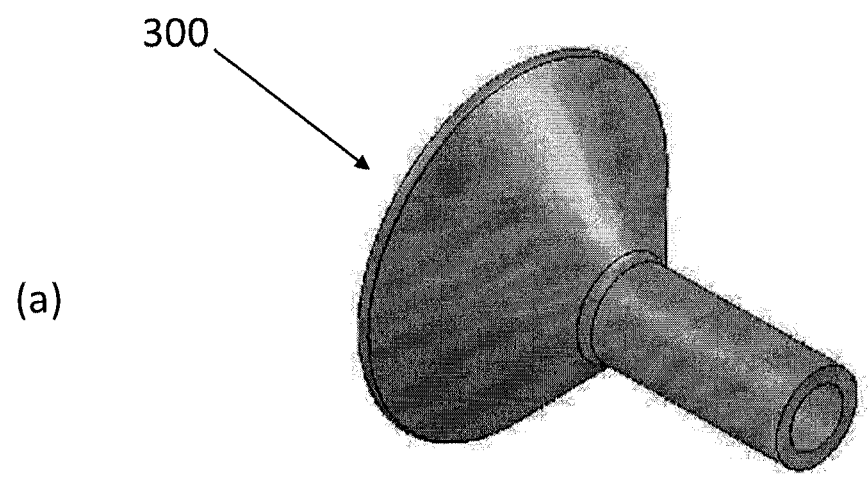

FIG. 7a and FIG. 7b shows a device according to one embodiment of the invention.

DETAILED DESCRIPTION OF THE INVENTION

The present invention relates to a catheter-based device and method for the evagination and the grasping, fixating and fastening (collectively referred to herein as "repositioning") of a body part. In a particularly important application, said body part is the intraatrial left atrial appendage (LAA). Although the invention is in no way limited to use in the LAA, this procedure will be used in the description to follow, to illustrate the device of the invention and its use.

The procedures described herein can be carried out under vision, employing vision techniques such as fluoroscopy and transesophageal echo.

In a specific embodiment of the invention, the device comprises an elongated flexible guide instrument, a suction device and a device suitable to deploy a fastening accessory. Other devices regularly used in endoscopic surgery, such as light sources, cameras etc. can be also carried in the guide instrument, and such conventional apparatus is not described herein in detail, for the sake of brevity.

In a particular embodiment of the invention, the suction device and the device to apply a fastening accessory are located in the lumen of the guide instrument. Said fastening accessory can be of any suitable type and can be made of one piece or of a plurality of pieces. In one embodiment of the invention, the fastening accessory comprises one or more clips. In another embodiment the fastening accessory comprises one or more loops. Different fastening accessories can also be combined and various suitable accessories will be easily evident to the skilled person from the description to follow.

Figure 1:
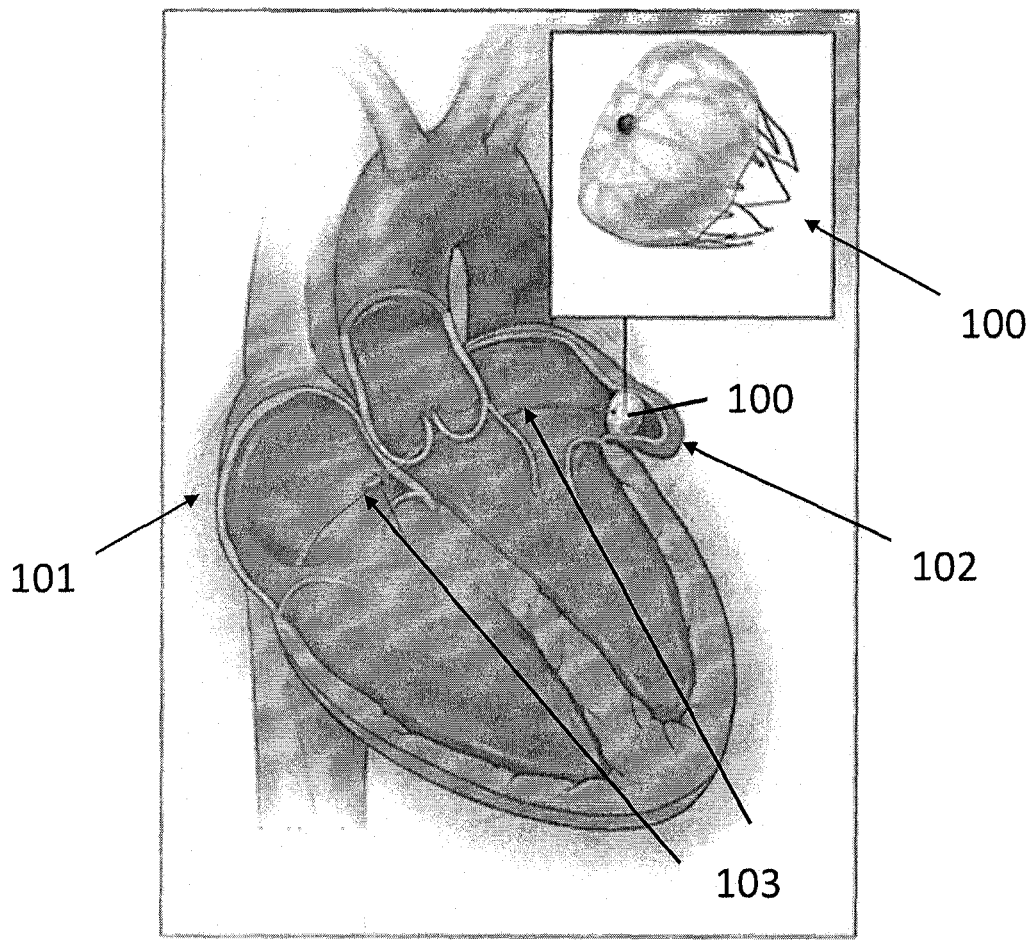
FIG. 1 illustrates the insertion of a prior art Watchman occlusion device into the LAA.

Transapex or transaortal or transatrial external through the pericard Transseptal access to the LLA is usually achieved by introducing a transseptal catheter through the femoral or jugular vein, and advancing the catheter transluminally into the right atrium. After locating the catheter in the right atrium, a long hollow needle is inserted transseptally by force through the fossa ovalis until attaining the left atrium, as seen at 100 in FIG. 1, with reference to the prior art method. Once in the left atrium, the catheter is advanced up to the LAA while monitored by any suitable method, such as echo- and/or fluoroscopic control. The device of the current invention is preferably inserted transseptally.

In one embodiment of the invention the catheter is provided at its tip with a suction channel that terminates in a concave holder selected from a cup, a cone or other semi-spherically shaped device, which is expanded after reaching the left atrium, thus preventing possible atrial and/or appendage wall perforation by the catheter tip. The suction channel can also be used for aspiring blood clots, especially those located in the LAA. Alternatively, a catheter tip can be made of any soft material that is less prone to cause perforation. As will be apparent to the skilled person, this safety feature (or an alternative one) is desirable but the invention can be carried out without it. The catheter is then inserted into the LAA (FIG. 2). Insertion of the catheter can again be guided by any suitable method, such as echo- and/or fluoroscopic control, direct or indirect vision, etc. Once the catheter is located in the LAA and touches the wall of the LAA, suction is applied through a channel connected with tip 201 (FIG. 3), such that tip 201 of catheter 202 holds portion 203 of the left atrial appendage 204 by suction. Thereafter, the catheter is pulled back into the left atrium under guided control, thus repositioning the left atrial appendage 204 into the left atrium (FIGS. 4a and 4b). The repositioned appendage at this time is held by suction. A fastening accessory is applied to the intraluminar base (FIGS. 5a and 5b) of the repositioned left atrial appendage, to permanently prevent its return in the normal position. The fastening accessory can be a clip, suture or loop 206, or an accessory combining a clip and a loop, or any other suitable fastening means. In the example of the loop, suitable arrangements are provided, e.g., a screw assembly, to detach it from its guide 205 after fastening is completed. After applying the fastening accessory, suction can be discontinued and the catheter removed (FIGS. 6a and 6b).

At the end of the procedure the LAA is repositioned into the left atrium and held by a fastening accessory. When operating according to the embodiment described above, as well as with other embodiments of the invention, no pins, hooks or other sharp and penetrating parts on the atrial wall are used, and no penetration of atrial wall outside to pericardium is performed.

When operating according to the invention, suction, of up to 1 atmosphere can be employed without substantial fear of damage to the tissue. The force applied to fixate the appendage base with a lasso or clip must be calculated so as not to impart damage. For instance, said force can be up to 3 kg, preferably 2 kg, provided the wire of lasso is at least 0.7 mm nitinol in diameter and the clip bar of the similar size at least are safe.

FIG. 7a and FIG. 7b illustrates the actual size of the suction device employed in in vivo experiments carried out with a pig heart. Pig hearts carry substantial similarity to human hearts in respect of the LAA problem and, therefore, were selected form the experiment.

Experimental Procedure and Selection of Operating Conditions

The above-illustrated procedure was carried out, in vivo, using a nitinol wire of 0.7 mm diameter as a lasso that created the loop 206 of the figures. As said, forces of 2-3 Kg were applied without any damage to the LAA tissue. However, should a practitioner wish to employ different operating conditions than the above, the following procedure should be followed:

1. Selection of Standard Substrate

A standard substrate, such as a silicone cylinder of 1 cm diameter is selected. Any other suitable soft material can be employed.

2. Determination of Standard Penetration Depth

The standard penetration depth with the selected material is determined by wrapping a lasso made of 0.7 mm diameter nitinol wire and applying a force of 2 Kg on the wire. When application of the force is completed the wire is removed and the depth to which it has penetrated the selected standard substrate is measured.

3. Determination of Alternative Operating Conditions

To determine a suitable set of operating conditions with a different type of wire, the selected wire is wrapped around the selected standard substrate as in 2 above, and forces of different magnitude are applied. The depth of penetration with each force applied is then measured. The force to be used with the newly selected wire is that which created a penetration depth essentially of the same magnitude as obtained in (2) above.

In an alternative embodiment of the invention fastening means are used, which are not integral with the guide introduced into the heart. In such a device the fastening means comprise filling means suitable to fill the void created in the outer part of a heart, by the repositioning of the left atrial appendage of the heart. Such filling means comprise, e.g., a biocompatible glue.

An alternative fixation method involves fixating the evaginated appendage in its position achieved after suction and traction, by anchoring it to the cardiac wall, for example to the interatrial septum.

In an alternative embodiment of the invention the device of the invention can be used in endoscopy of gastrointestinal, urinary, airway or any other tract to grasp (with suction) and to put a loop (clip) on polyps, tumors etc. Such uses also form a part of the invention.

The skilled person will devise many other additional uses of the device of the invention. For instance, suction can be applied through the suction channel to remove blood clots from the LAA, prior to any other operations.

As will be apparent to the skilled person from the above description, the invention affords the means for performing an effective and safe procedure, which was not available in the art before the invention. Although the invention has been described using a preferred embodiment by way of illustration, the skilled person will easily appreciate the many alternative ways in which the invention can be carried out.

The invention claimed is:

1. A completely atraumatic method for repositioning a left atrial appendage (LAA) of a heart, comprising:
    transseptally and transvascularly introducing a guide instrument within a human body; wherein said guide instrument comprising a suction channel passing through a lumen of said guide instrument terminating with a concave holder, said suction channel and said concave holder are enclosed within said lumen of said guide instrument during said introducing;
    distally positioning said guide instrument in a left atrium (LA) distal to an ostium of said LAA;
    extending said suction channel and radially expanding said concave holder from said lumen of said guiding instrument into said LAA;
    holding a portion of the LAA by said concave holder by applying suction through said suction channel without imparting damage to the LAA, until said portion of the LAA is held and drawn into a lumen of said concave holder;
    fully inverting said held LAA portion into said LA while said held LAA portion is outside said lumen of said guide instrument;
    extending forward and expanding a fastener from said lumen of said guide instrument, wherein said fastener is shaped and sized to be enclosed within said lumen of said guide instrument during said introducing; and
    fastening said fully inverted LAA portion by said fastener;
    wherein all of said steps being performed without imparting damage to the LAA,
    and
    wherein said fastening comprising actuating said fastener from within said lumen of said guide instrument in such a way to be wrapped around said fully inverted LAA portion to permanently prevent return thereof to its normal position and to close said LAA.

2. A method according to claim 1, wherein the fastener is applied to the inverted LAA portion by a force of up to 3 kg, without imparting damage to the LAA.

3. A method according to claim 1, wherein the concave holder is expanded from within said lumen of said guide instrument to achieve a concave configuration after reaching the LA to prevent atrial or appendage wall perforation.

4. A method according to claim 1, wherein the guide instrument is introduced through a femoral or jugular vein, transluminally to a right atrium, and transseptally through a fossa ovalis until assessing the LAA.

5. A method according to claim 1, wherein suction of up to 1 atmosphere is applied through the suction channel without imparting damage to the LAA.

6. A method according to claim 1, wherein a distal dimension of the concave holder lumen is significantly greater than its proximal dimension, and the distally positioning is performed by distally positioning the guide instrument until the concave holder is centered with respect to, and in close juxtaposition with, a cavity wall at an apex of the LAA.

7. A method according to claim 6, wherein the fastener comprises a guide disposed internally within the guide instrument; a string or a flexible looped element received within, and attached to, said guide; and an actuator,
    wherein said string or flexible looped element, when actuated, is discharged from a distal end of said guide and is caused to completely encircle the concave holder and an intraluminar base of the drawn LAA portion until fastening is completed, to permanently prevent return of the drawn LAA portion to its normal position.

8. A method according to claim 1, wherein the guide instrument is distally positioned until the concave holder contacts a LAA cavity wall.

9. A method according to claim 1, wherein said expanding and extending comprises extending forward said fastener over and beyond said concave holder.

10. A method according to claim 1, wherein said fastening comprises fastening said fully inverted LAA portion by said fastener while said fully inverted LAA is outside said lumen of said guide instrument.

* * * * *